United States Patent [19]

McDonald

[11] Patent Number: 5,171,228
[45] Date of Patent: * Dec. 15, 1992

[54] APPARATUS FOR MEDICAL INSTRUMENT PLACEMENT VERIFICATION

[75] Inventor: Ray S. McDonald, St. Paul, Minn.

[73] Assignee: Medtronic, Inc., Minneapolis, Minn.

[*] Notice: The portion of the term of this patent subsequent to Apr. 23, 2008 has been disclaimed.

[21] Appl. No.: 631,568

[22] Filed: Dec. 21, 1990

Related U.S. Application Data

[63] Continuation-in-part of Ser. No. 385,132, Jul. 25, 1989, Pat. No. 5,009,644.

[51] Int. Cl.$^5$ .............................................. A61M 5/32
[52] U.S. Cl. .................................. 604/175; 604/93; 604/116
[58] Field of Search ............... 604/93, 116, 117, 175, 604/891.1

[56] References Cited

U.S. PATENT DOCUMENTS

| 4,216,775 | 8/1980 | Cottingham | 128/303.18 |
|---|---|---|---|
| 4,494,950 | 1/1985 | Fischell | 604/66 |
| 4,692,146 | 9/1987 | Hilger | 604/93 |
| 4,760,837 | 8/1988 | Petit | 128/1 R |
| 4,784,646 | 11/1988 | Feingold | 604/175 |
| 4,804,054 | 2/1989 | Howson et al. | 128/898 |
| 4,871,351 | 10/1989 | Feingold | 604/66 |
| 5,006,115 | 4/1991 | McDonald | 604/175 |
| 5,009,644 | 4/1991 | McDonald | 604/175 |

FOREIGN PATENT DOCUMENTS

| 0245132 | 4/1987 | European Pat. Off. |
| 0300552 | 7/1988 | European Pat. Off. |
| 0322978 | 12/1988 | European Pat. Off. |

OTHER PUBLICATIONS

Advertisement for Cell Control Device (discussed within the specification).

Primary Examiner—Gene Mancene
Assistant Examiner—Cindy A. Cherichetti
Attorney, Agent, or Firm—Harold R. Patton; Terry L. Wiles

[57] ABSTRACT

An apparatus for verifying the proper placement of a medical instrument, such as a needle, with respect to an implantable medical device, such as a drug dispensing port or pump. The apparatus includes an internal circuit which is implantable within the body tissue, and an external circuit for communicating with the internal circuit. The internal circuit includes an electrically conductive plate for sensing proper contact between the medical instrument and the medical device. A resonant circuit is coupled between the plate and the body tissue, and has a predetermined resonance frequency, such that an electrical path is established through the resonant circuit, the plate, the body tissue and the medical instrument when the medical instrument is in proper contact with the medical device. The external circuit includes a transmitter circuit for sending signals either pulsed or continuous to the resonant circuit. The transmitted signals have a frequency equal to the resonance frequency, for causing the resonance circuit to resonate when the medical instrument is not properly placed with the respect to the implantable medical device. A receiver circuit detects the resonance signals generated by the resonant circuit, and an alarm circuit responds to the receiver circuit for generating an appropriate alarm signal.

7 Claims, 2 Drawing Sheets

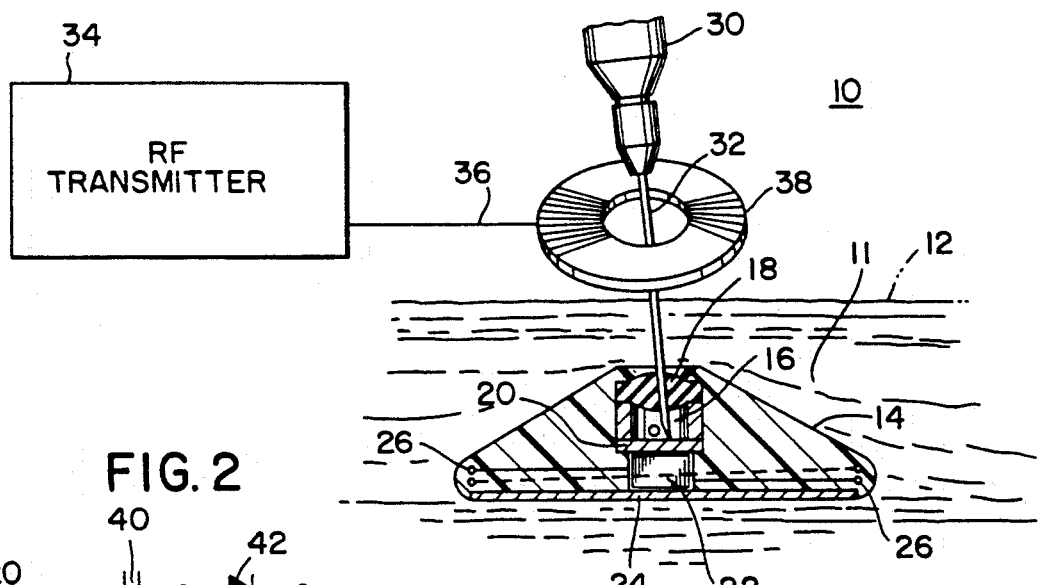
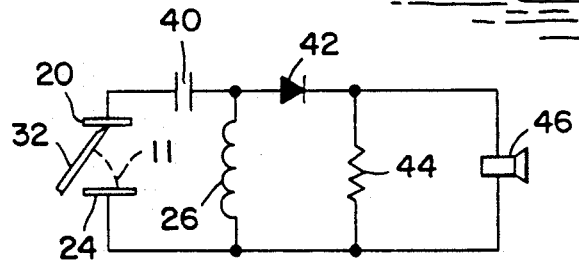
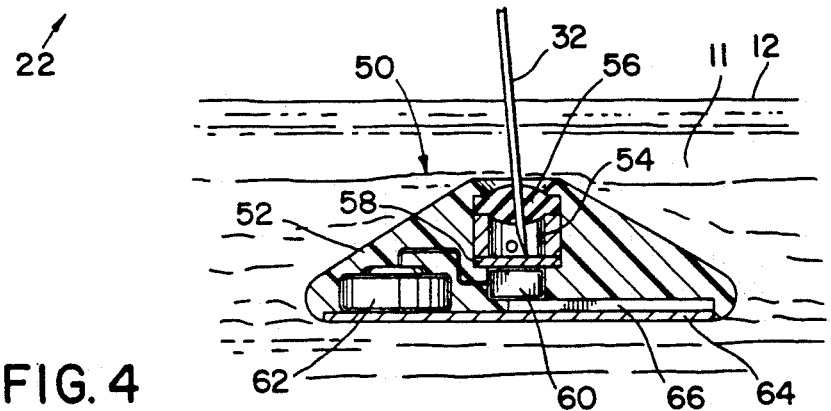
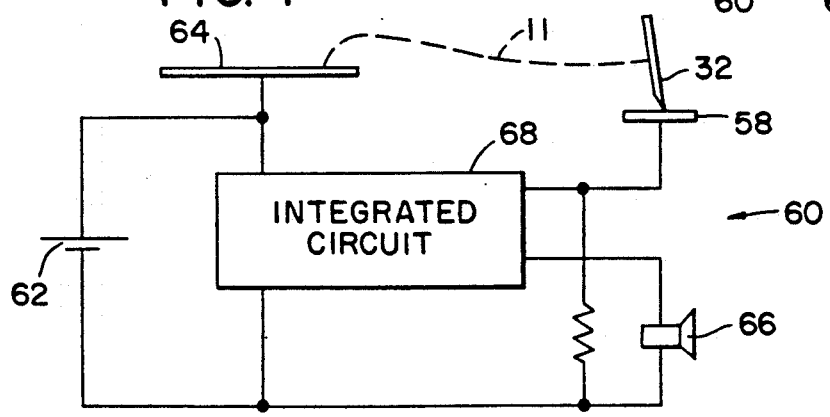

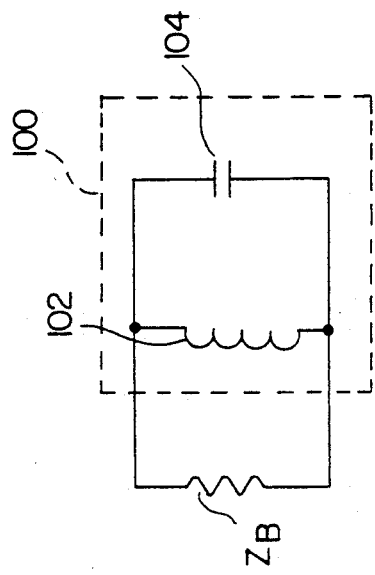
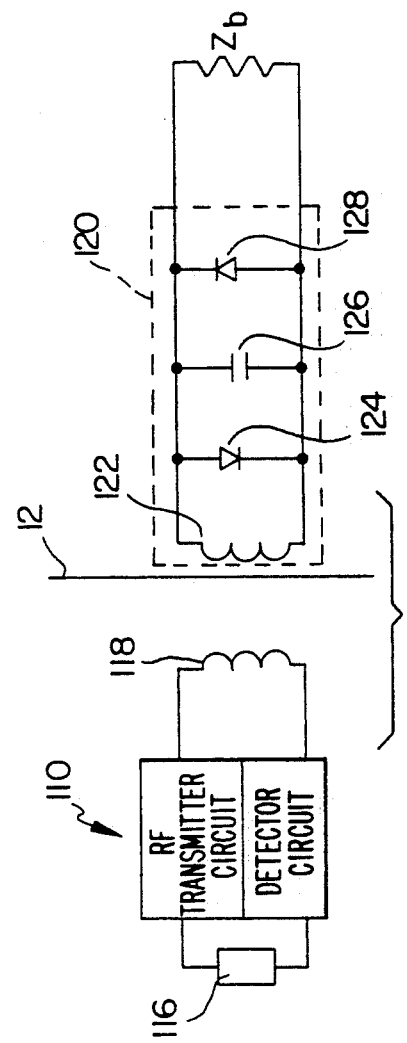
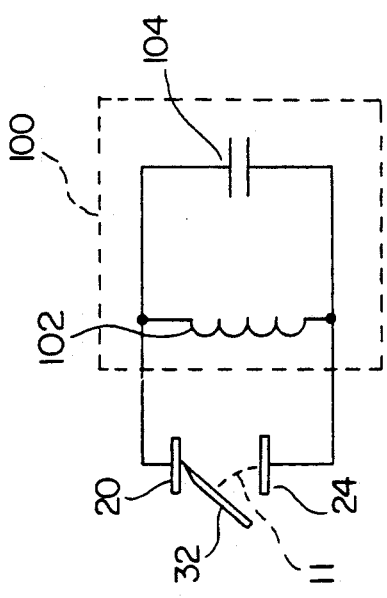
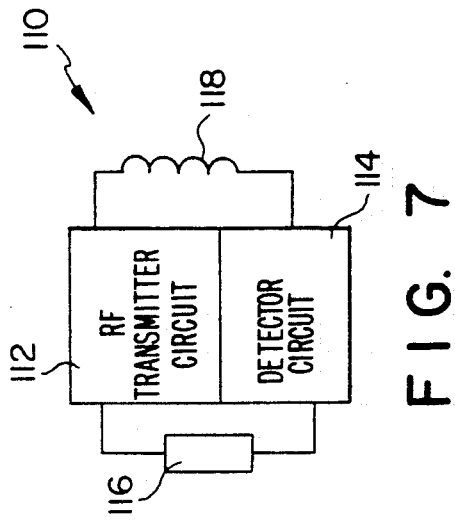

APPARATUS FOR MEDICAL INSTRUMENT PLACEMENT VERIFICATION

This is a continuation-in-part of the co-pending U.S. patent application Ser. No. 07/385,132, filed Jul. 25, 1989, now U.S. Pat. No. 5,009,644.

BACKGROUND OF THE INVENTION

Many implantable medical devices require percutaneous communication. For example, devices which dispense drugs within the body require a supply provided by hypodermic needle injection through the skin. In devices such as implantable drug dispensers or catheter access ports, a needle is inserted through the skin, through a piereable septum on the drug dispenser, and into a reservoir where the drug is to be injected.

Since the medical device is installed subcutaneously, care must be taken to make sure that the needle is properly placed into the device before injection. If the needle misses the device, drug will be dispensed in the body either in an improper location or in improper amounts. If the needle does not properly peirce the septum, drug will not be dispensed adequately into the desired reservoir location.

Previous attempts have been made to provide notification of needle placement. These have involved complex apparatus such as the Celcontrol brand detector which requires the attachment of an electrode to the skin and the attachment of a wire to complete the circuit to the hypodermic needle. What is needed is a simpler technique for sensing needle position which does not require attachments to the skin or needle.

SUMMARY OF THE INVENTION

Therefore, it is an object of the present invention to address the above concerns, and to provide adequate solutions thereto. Briefly, the above and further objects and features of the present invention are realized by providing a new apparatus for verifying the proper placement of a medical instrument, such as a needle, with respect to an implantable medical device, such as an drug dispensing port or pump.

The apparatus includes an internal circuit which is implantable within the body tissue, and an external circuit for communicating with the internal circuit. The internal circuit includes an electrically conductive plate for sensing proper contact between the medical instrument and the medical device.

A resonant circuit is coupled between the plate and body tissue, and has a predetermined resonance frequency, such that an electrical path is established through the resonant circuit, the plate, the body tissue and the medical instrument when the medical instrument is in proper contact with the medical device. The external circuit includes a transmitter circuit for sending signals either pulsed or continuous, to the resonant circuit. The transmitted signals have a frequency equal to the resonance frequency, for causing the resonance circuit to resonate when the medical instrument is not properly placed with respect to the implantable medical device.

A receiver circuit detects the resonance signals generated by the resonant circuit, and an alarm circuit responds to the receiver circuit for generating an appropriate alarm signal.

BRIEF DESCRIPTION OF THE DRAWINGS

FIG. 1 is a system view, partly schematic, of an implantable apparatus constructed according to the present invention including an external RF transmitter in a hypodermic needle;

FIG. 2 is a schematic of a sample circuit for the device of FIG. 1;

FIG. 3 is a cross-sectional view of an alternative embodiment of the present invention;

FIG. 4 is a schematic view of the circuit of the device of FIG. 3;

FIG. 5 is a schematic representation of an alternative embodiment of a resonant implantable circuit for use in the apparatus of FIG. 1;

FIG. 6 is another schematic representation of the alternative embodiment of the implantable FIG. 5;

FIG. 7 is a schematic diagram of an external RF transmitter/detector for use in the apparatus of FIG. 1; and FIG. 8 is a schematic representation of yet another alternative embodiment of the implantable circuit of FIG. 1.

DETAILED DESCRIPTION OF THE PREFERRED EMBODIMENTS

The invention is illustrated by a catheter access port 10 implanted in tissue 11 below skin 12 of a patient. One skilled in the art may employ the present invention and other devices requiring percutaneous contact with medical instruments. Access port 10 includes a body 14 which has a fluid reservoir 16. Reservoir 16 is sealed off from the patient environment by pierceable septum 18. Access port 10 includes a contact plate 20 at the base of reservoir 16. Contact plate 20 is electrically connected to circuitry 22, shown schematically in FIG. 1. Circuitry 22 is electrically connected to conductive base plate 24 which is mounted on the outside of body 14. Embedded in body 14 and electrically connected to circuit 22 is coil or receiving antenna 26.

Access port 10 is used to transmit medicament through a portion of the body by a catheter. Medicament is added to reservoir 16 by a syringe 30 having a needle 32 which pierces skin 12 and septum 18. In the position illustrated, needle 32 is within reservoir 16 in contact With contact 20 and is prepared for drug injection.

In order for the sensing means of access port 10, including circuitry 22, contact plate 20 and common plate 22 to sense placement of needle 32, power must be available. In this embodiment, power is transmitted by radio frequency. RF transmitter 34 is shown schematically connected by wires 36 to transmitting antenna 38. Components 34-38 are well known prior art devices where may be employed in the practice of the present invention. Transmitter 34 could be any of the available prior art transmitters. A particular useful example would be the transmitter for the Medtronic Pisces brand spinal stimulation system.

Antenna 38 is shown as a circular disk with a central hole, but may be other suitable medical transmitting antennas. When transmitter 34 sends RF energy through antenna 38, it is received by receiving antenna 26 within access port 10.

Referring to FIG. 2, circuit 22 includes capacitor 40, diode 42, resistor 44 and piezoelectric beeper 46. Circuit 22 has capacitor 40 in series with coil 26. When no needle 32 is present, the only power present is the reactance of coil 26. Therefore, no activation of beeper 46 results. When needle 32 is inserted through septum 18 against contact 20, circuit 22 includes a parallel resonant circuit. The circuit is completed from the needle to the contact plate through circuitry 22 to the common plate 24 and back through the skin of the patient to needle 32.

In the completed circuit, capacitor 40 is placed in parallel across coil 26. The value of coil inductance and capacitance will resonate at a certain frequency. This is the frequency that is preferably delivered by antenna 38. Many frequencies may be used to employ the present invention. Preferably, energy should be broadcast in the 100-200 kHz region.

After rectification by diode 42, current is applied to piezobeeper 46 and sound is emitted. Piezobeeper 46 may be any of the well known piezo devices, such as a sound device in the Medtronic Synchromed brand drug dispensers.

The sound is preferably generated by bursts of energy from antenna 38. Envelopes of bursts are preferably transmitted. If energy is transmitted in pulses of a particular frequency, such as 500 Hz, there will be a tone of that frequency. Envelopes of bursts are sensed so that a tone will be heard for the duration of the envelope. Therefore, intermittent beeps will result.

In FIG. 3, an alternative embodiment shows catheter access port 50 having a body 52 with a reservoir 54 enclosed by septum 56, as discussed above. A contact plate 58 is located in the bottom on reservoir 54, as discussed above. Contact plate 58 is electrically connected to circuitry 60, which is illustrated schematically. Also connected to circuitry 60 is battery 62, indifferent plate 64, and beeper 66.

The embodiment of FIG. 3 operates in a manner similar to that of FIG. 1, except that power is provided internally by battery 62 so that no broadcast of RF energy is required. Circuit 60 includes integrated circuit 68 similar to integrated circuits commonly used for controlling light emitting diodes. Inside the integrated circuit 68 is an electrode called the switch or a gate which is a high impedance unit. The integrated circuit is assumed to be CMOS so that it has very small current drain when there is no circuit connection. The circuitry employed for this is well known in the art.

In FIG. 4, the circuit path, as discussed above, is from indifferent plate 64 through skin 12 to needle 32 and hence to contact 58. There is a potential voltage when the indifferent plate 64 is at the same potential as the contact 58. Integrated circuit 68 will then detect the fact that its gate is at the same potential and will start putting pulses from battery 62 to the piezobeeper 66. Sound will be emitted at the frequency of the pulses.

In this embodiment, the sound continues as long as the needle is in place and the drug is being administered. When the needle is removed, the circuit will go to low power and the device will wait for the next needle insertion. In alternative embodiments, the tone can be emitted for a time period and then shut off so that the tone is not continually sounding the whole time the needle is in the septum. While the invention is illustrated in terms of a catheter access port of the particular embodiment, it is understood that those skilled in the art can practice the invention to other various devices and embodiments.

Referring now to FIG. 5, there is illustrated an alternative embodiment 100 of the implantable circuit 22 of FIG. 1. The implantable circuit 100 includes a resonant circuit such as an inductor 102 and a capacitor 104 connected in parallel. The implantable circuit 100 is used in conjunction with the external RF transmitter/detector 110 which is described below in connection with FIG. 7.

In operation, the RF transmitter/detector 110 replaces the RF transmitter 34 of FIG. 1, and is used to transmit energy to the implanted circuit 100, and to detect the response signal generated by the implanted circuit 100. When the needle 32 is not properly positioned with respect to the plate 20, the circuit 20 resonates in response to the RF energy generated by a transmitter circuit 112 of the external transmitter/detector 110. The resonance signals of the circuit 20 are detected by a detector circuit 114, and a visual and/or audible alarm circuit 116 is actuated for indicating that the needle 32 has not been properly positioned with the catheter access port 10.

If on the other hand, the needle 32 is properly positioned in contact with the plate 20, the body impedance illustrated by the reference $Z_b$ in FIG. 6, shunts the resonance circuit 100 and prevent the implanted circuit 100 from resonating at peak energy. As a result, the detector circuit 114 detects a weak response signal from the resonance circuit 100.

Consequently, the present invention relates to an efficient verification system including an external RF transmitter 112 and an implantable circuit 100 for verifying the placement of the needle 32 within the catheter access port 10. One advantage of the verification system is that the implanted circuit 100 does not include a power source, such as a battery cell. Hence, the reliability of the verification system is enhanced, and its longetivity is increased.

Additionally, the external alarm system 116 is operated by a high energy source, and as such it will generate clearer and louder alarm signals, than those generated by an implantable alarm device.

Considering now the RF transmitter/detector 110 in greater detail in connection with FIG. 7, it generally includes an induction coil 118 for transmitting energy to, and receiving response resonance signals from the implanted circuit 100. The induction 118 could include the antenna 38 or, in the alternative, a conventional telemetry induction coil.

The RF transmitter circuit 112 is similar to the RF transmitter 34 described above in connection with FIG. 1. The detector circuit 114 is tuned to detect signals having a frequency substantially equal to the resonance frequency of the implanted circuit 100.

Considering now the implanted circuit 100 in greater detail, in connection with FIG. 6, it is generally coupled to the body impedance $Z_b$. As illustrated, the body impedance is connected in parallel with the inductance 102 and the capacitor 104 such that, when the needle 32 is not properly positioned with respect to the plate 20, the Q value of the implanted circuit 100 is high, and the circuit 100 will ring at its resonant frequency.

The detector circuit 114 has a receiver (not shown) which detects the ringing or resonance signal sets reference received amplitude, and actuates the alarm circuit 116, for causing it to generate an audible, visual or similar alarm signals, to indicate that the position of the needle 32 is not acceptable and requires adjustment.

If on the other hand, the needle 32 is properly positioned, then the effective body impedance $Z_b$ will be relatively low, and will substantially shunt the resonance circuit 100, hence reducing its effective Q value. The detector circuit 114 senses that the peak value of the signals received from the implanted circuit 100 is lower than the established reference received amplitude which was set up when the needle was not yet in proper position, and consequently, it will cause the alarm circuit 116 to give a corresponding indication.

It should become apparent to those skilled in the art after reviewing the above description that the contact plate 20 could be disposed in series with the resonance circuit 100, rather than in parallel, as shown in FIG. 5, such that the electrical circuit is closed, and the resonant circuit 100 will ring upon the proper placement of the needle 32 in contact with the plate 20.

FIG. 8 is a schematic representation of yet another alternative embodiment 120 of the implanted circuit 22. The implanted circuit 120 is shown inductively coupled to the RF transmitter/detector 110. In this embodiment, the implanted circuit 120 includes two diodes 122 and 128 coupled in parallel with a capacitance 126 and an inductance 124 to allow condition in both directions. This configuration causes harmonic energy to be generated and received by the RF transmitter/detector 110.

When the needle 32 is properly positioned, the body impedance $Z_b$ causes the implanted circuit 120 to become lossy, and the amplitude of the resonance signals remains below the threshold value of the diode. Consequently, no harmonic energy will be transmitted to the RF transmitter/detector 110.

While the present invention is described in connection with a drug dispensing device such as a catheter access port, it should become apparent to those skilled in the medical art that the present invention has other applications in the field of implantable medical devices. It is also to be understood that various different modifications are possible and are contemplated within the scope of the specification, drawings, abstract and appended claims.

What is claimed is:

1. An apparatus for verifying the proper placement of a medical instrument with respect to an implantable medical device, the apparatus comprising:
   A. internal circuit being implantable within the body tissue;
   B. external circuit for communicating with said internal circuit;
   C. said internal circuit including:
      a. means for sensing proper contact between the medical instrument and the medical device; and
      b. resonant circuit coupled between said sensing means and the body tissue, said resonant circuit having a predetermined resonance frequency, such that an electrical path is established through said resonant circuit, said sensing means, the body tissue and the medical instrument when the medical instrument is in proper contact with the medical device; and
   D. said external circuit including:
      a. transmitter circuit for sending signals to said resonant circuit, said signals having a frequency substantially equal to said resonance frequency, for causing said resonance circuit to generate resonance signals when the medical instrument is not properly placed with respect to the implantable medical device;
      b. receiver circuit for detecting said resonance signals generated by said resonant circuit; and
      c. alarm circuit responsive to said receiver circuit for generating an alarm signal.

2. The apparatus as defined in claim 1, wherein said resonant circuit includes an inductive an a capacitive elements.

3. The apparatus as defined in claim 2, wherein said resonant circuit includes at least one diode coupled in parallel to said inductive and capacitive elements for preventing conduction below a predetermined threshold level.

4. The apparatus as defined in claim 3, wherein said sensing means includes an electrically conductive plate, and wherein said alarm signal is an audible signal.

5. The apparatus as defined in claim 1, wherein said sensing means includes an electrically conductive plate.

6. The apparatus as defined in claim 4, wherein said alarm signal is a visual signal.

7. An apparatus for verifying the proper placement of a medical instrument with respect to an implantable medical device, the apparatus comprising:
   A. internal circuit being implantable within the body tissue;
   B. external circuit for communicating with said internal circuit;
   C. said internal circuit including:
      a. means for sensing proper contact between the medical instrument and the medical device; and
      b. resonant circuit coupled between said sensing means and the body tissue, said resonant circuit having a predetermined resonance frequency, such that an electrical path is established through said resonant circuit, and sensing means, the body tissue and the medical instrument when the medical instrument is in proper contact with the medical device; and
   D. said external circuit including:
      a. transmitter circuit for sending signals to said resonant circuit, said signals having a frequency substantially equal to said resonance frequency, for causing said resonance circuit to generate resonance signals when the medical instrument is properly placed with respect to the implantable medical device;
      b. receiver circuit for detecting said resonance signals generated by said resonant circuit; and
      c. alarm circuit responsive to said receiver circuit for generating an alarm signal.

* * * * *